United States Patent
McQuade et al.

(10) Patent No.: US 9,951,020 B2
(45) Date of Patent: Apr. 24, 2018

(54) METHODS OF MAKING 2-HALONICOTINONITRILES

(71) Applicants: D. Tyler McQuade, Tallahassee, FL (US); Frank B. Gupton, Tallahassee, FL (US); Ashley R. Longstreet, Tallahassee, FL (US); Suzanne M. Opalka, Tallahassee, FL (US)

(72) Inventors: D. Tyler McQuade, Tallahassee, FL (US); Frank B. Gupton, Tallahassee, FL (US); Ashley R. Longstreet, Tallahassee, FL (US); Suzanne M. Opalka, Tallahassee, FL (US)

(73) Assignees: Virginia Commonwealth University, Richmond, VA (US); The Florida State University Research Foundation, Incorporated, Tallahassee, FL (US)

(*) Notice: Subject to any disclaimer, the term of this patent is extended or adjusted under 35 U.S.C. 154(b) by 0 days.

(21) Appl. No.: 15/048,319

(22) Filed: Feb. 19, 2016

(65) Prior Publication Data
US 2016/0221951 A1  Aug. 4, 2016

Related U.S. Application Data

(63) Continuation-in-part of application No. PCT/US2014/053344, filed on Aug. 29, 2014.

(60) Provisional application No. 61/871,496, filed on Aug. 29, 2013.

(51) Int. Cl.
| | |
|---|---|
| *C07D 213/85* | (2006.01) |
| *C07D 217/26* | (2006.01) |
| *C07D 221/10* | (2006.01) |
| *C07D 221/16* | (2006.01) |
| *C07D 409/04* | (2006.01) |

(52) U.S. Cl.
CPC ......... *C07D 213/85* (2013.01); *C07D 217/26* (2013.01); *C07D 221/10* (2013.01); *C07D 221/16* (2013.01); *C07D 409/04* (2013.01)

(58) Field of Classification Search
CPC .................................................. C07D 213/85
See application file for complete search history.

(56) References Cited

U.S. PATENT DOCUMENTS 2,491,253 A  12/1949  Crossley et al.

FOREIGN PATENT DOCUMENTS

| CN | 103508945 A | 1/2014 |
| WO | 2001/025207 A1 | 4/2001 |

OTHER PUBLICATIONS

Raghukumar et al., 'Synthesis of nicotinontrile derivatives as a new class of NLO materials', Tetrahedron 59 (2003) 3761-3768.
Longstreet et al., 'Improved Synthesis of Mono- and Disubstituted 2-Halonicotinontriles from Alkylidene Malononitriles', Org. Lett., 2013, 15 (20), pp. 5298-5301 (Publication Date (Web): (Oct. 4, 2013).
Kuyper L F et al: "Pyrrolo[2,3-d]pyrimidines and oyrido [2,3-d] pyrimidines as conformationally restricted analogues of the antibacterial agent trimethoprim", Bioorganic & Medical Chemistry, Pergamon, GB, vol. 4, No. 4, Apr. 1, 1996, pp. 593-602.
Rolf H Pragev et al: "A Simple Synthesis of Amphimedine" Aust. J. Chem, Jan. 1, 1991, pp. 277-285.
Ida Nymann Petersen et al: "Total synthesis of ascididemin via anionic cascade ring closure", Chemical Communications—CHEMCOM., vol. 48, No. 72, Jan. 1, 2012, pp. 9092-9094.
Ashley R Longstreet et al: "Investigating the continuous synthesis of a nicotinonitrile precursor to nevirapine", Beilstein Journal of Organic Chemistry, vol. 9, Nov. 20, 2013, pp. 2570-2578.
Ashley R Longstreet et al: "Synthesis and Reactivity Profile of Ylidenemalononitrile Enamies and Their Ester Analogs Towards Electrophiles and Nucleophiles", vol. 80, No. 17, Sep. 4, 2015, pp. 8583-8596.

*Primary Examiner* — Noble E Jarrell
*Assistant Examiner* — John S Kenyon
(74) *Attorney, Agent, or Firm* — Whitham, Curtis & Cook, P.C.

(57) ABSTRACT

A method of making a 2-halonicotinonitrile comprises reacting an alkylidene nitrile with a C1-compound in an organic solvent and a dehydrating agent. The dehydrating agent substantially retards dimerization of the alkylidene nitrile during the reaction. The enamine intermediate that forms from the reaction is cyclized using a halide donor to make the 2-halonicotinonitrile.

22 Claims, 1 Drawing Sheet

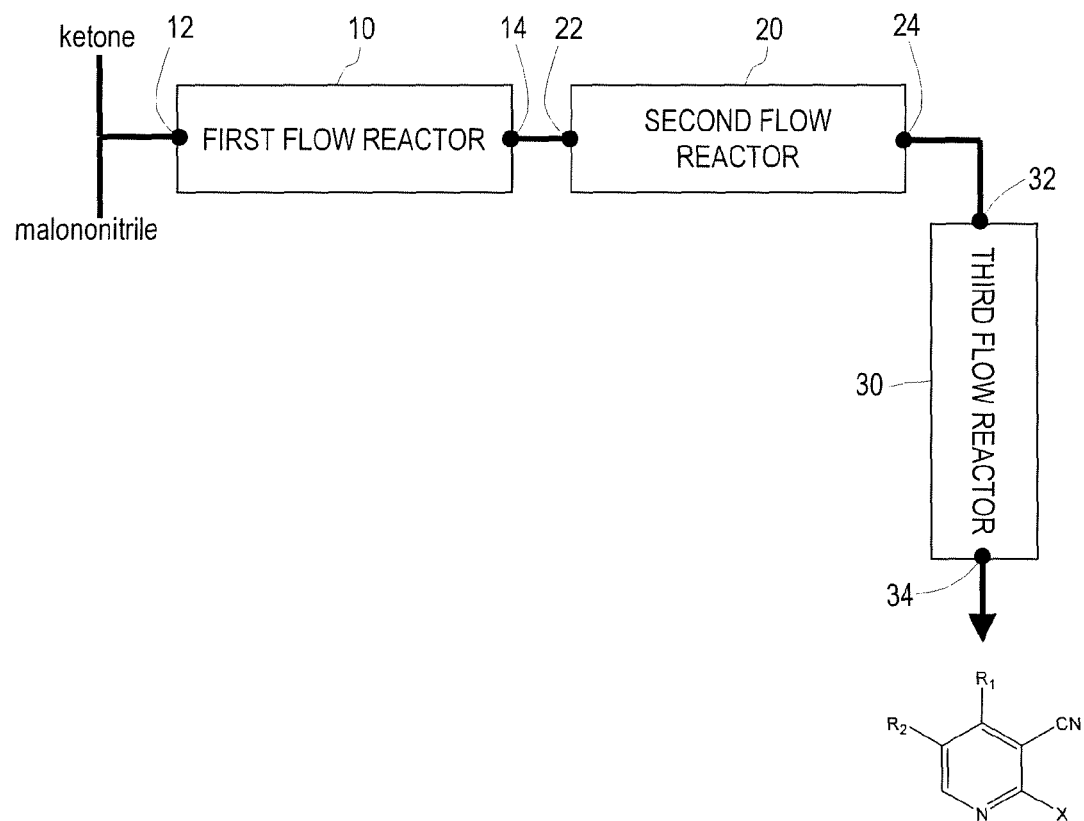

METHODS OF MAKING 2-HALONICOTINONITRILES

CROSS-REFERENCE TO RELATED APPLICATIONS

This application is a Continuation in Part of PCT/US2014/053344, filed Aug. 29, 2014, which claims priority to U.S. provisional Application No. 61/871,496, filed Aug. 29, 2013, which is incorporated by reference in its entirety.

FIELD OF THE INVENTION

This relates to the field of synthesizing substituted pyridine compounds. More particularly, this relates to synthesizing halo-substituted nicotinonitriles.

BACKGROUND

Polysubstituted and fused pyridines are widely used chemicals. They are pharmaceutical active ingredients, biological markers, and starting ingredients in pharmaceutical synthesis. Unfortunately, however, it is difficult to synthesize them in high yields. Pyridines substituted at the 2, 3, 4 and 2, 3, 4, 5 positions are particularly valuable, but very few of the conventional techniques for pyridine substitution actually lead to 2, 3, 4 or 2, 3, 4, 5 substituted pyridines.

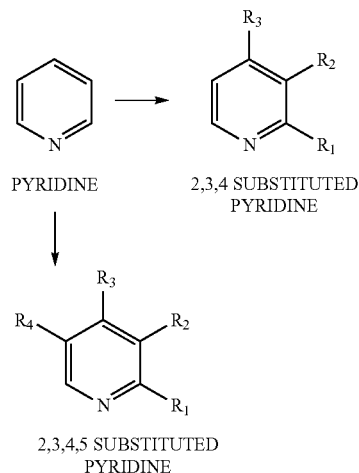

Baldwin, Raab, and Ponticello (BRP) previously developed a scheme to synthesize substituted 2-bromonicotinonitriles from alkylidene malononitriles using N,N-dimethylformamide dimethyl acetal (DMF-DMA). Scheme 1 illustrates the BRP synthesis from an alkylidene malononitrile to a 4,5-substituted-2-bromonicotinonitrile.

Scheme 1.

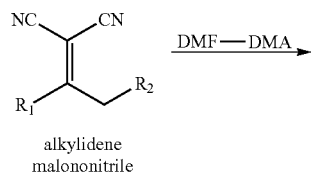

alkylidene malononitrile

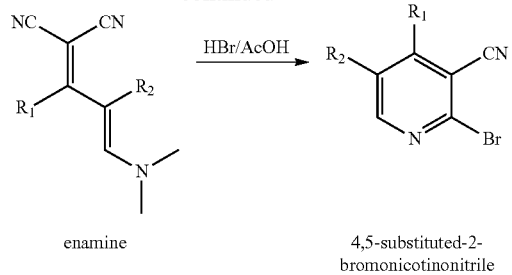

enamine    4,5-substituted-2-bromonicotinonitrile

The BRP synthesis works, but the yield is not ideal for synthesis of nicotinonitriles in commercial yields. We ascribe the yield of the BRP synthesis to dimerization of the alkylidene malononitrile starting ingredient.

SUMMARY

We developed new methods of making 2-halonicotinonitrile compounds using an alkylidene nitrile as a starting ingredient. By incorporating a dehydrating agent in the synthesis of 2-halonicotinonitriles we substantially retard dimerization of the alkylidene nitrile. Retarding dimerization of the alkylidene nitrile substantially improves the yield of 2-halonicotinonitriles relative to conventional synthetic methods.

A method of making a 2-halonicotinonitrile comprises (a) reacting an alkylidene nitrile having the formula of compound 1 with a C1-compound in an organic solvent and sufficient dehydrating agent to substantially retard dimerization of the alkylidene nitrile during the reaction, thereby forming an enamine intermediate; and (b) cyclizing the enamine intermediate with a halide (X) donor, thereby forming a 2-halonicotinonitrile having the formula of compound 3.

The dehydrating agent may be at least one dehydrating agent selected from an anhydride, an acetyl chloride, an aluminum trichloride, a thionyl chloride, an alkyl arylsilyl chloride, and a trialkyl arylsilyl chloride.

The C1-compound may be least one compound selected from N,N-dimethylformamide dimethylacetal, a formate, a formaldehyde, N,N-dimethylformamide methyl methylsufonylacetal, a methyl formate, and carbon monoxide.

The organic solvent may be least one organic solvent selected from dichloromethane, toluene, tetrahydrofuran, an ether, ethyl acetate, and chloroform.

The halide donor may be least one halide donor selected from a hydrogen halide, an alkyl halide, and a silyl halide. Preferred halides (X) are Br, Cl, or I.

The amount of dehydrating agent sufficient to substantially retard dimerization of the alkylidene nitrile during the reaction is 10 mol % to 200 mol % of dehydrating agent.

The C1-compound may be present in stoichiometric excess relative to the alkylidene nitrile.

The method may be performed under batch or flow conditions. A particular flow-based method of making a 2-halonicotinonitrile comprises synthesizing an alkylidene malononitrile having the formula of compound 1a by flowing a ketone and malononitrile through a first flow reactor containing a drying agent; (b) reacting, by flowing through a second flow reactor, the alkylidene malononitrile, a C1-compound, an organic solvent, and sufficient dehydrating agent to substantially retard dimerization of the alkylidene malononitrile during the reaction, thereby forming an enamine intermediate; and (c) cyclizing the enamine intermediate with a halide (X) donor, thereby forming a 2-halonicotinonitrile having the formula of compound 3a.

BRIEF DESCRIPTION OF THE DRAWINGS

FIG. 1. Schematic representation of exemplary flow reactors for performing methods described herein.

DETAILED DESCRIPTION OF PREFERRED EMBODIMENTS

An embodiment of the method of making a 2 halonicotinitrile is generally illustrated in Scheme 2.

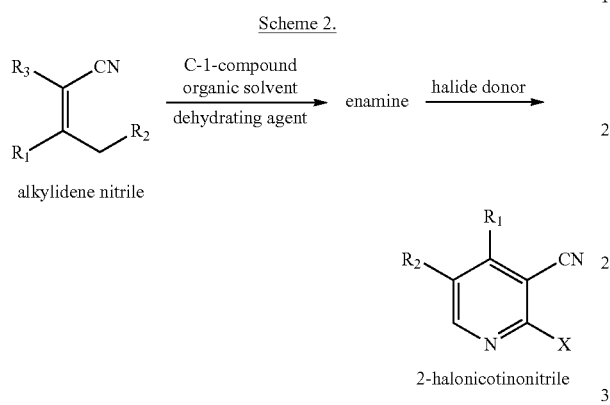

In the first reaction, the alkylidene nitrile starting ingredient is reacted with a C1-compound in a solution containing an organic solvent. The solution also contains sufficient dehydrating agent to substantially retard dimerization of the alkylidene nitrile during this reaction. The reaction forms an enamine intermediate. The enamine then cyclized to form a 2-halonicotinonitrile by reacting the enamine with a halide donor.

The abbreviations used in Scheme 2 are those typically used in organic chemical synthesis. $R_1$, $R_2$, and $R_3$ represent generic functional groups. They may be the same or they may be different, depending on the 2-halonicotinonitrile product one desires to make. Exemplary R1 functional groups include but are not limited to: lower alkyl groups (e.g. about C1 to about C5 alkyl) which may be branched or unbranched, and may be substituted or unsubstituted; lower alkenes (e.g. about C1 to about C5) which may be branched or unbranched, and may be substituted or unsubstituted; 5 and 6 membered carbon rings which may be saturated or unsaturated, substituted or unsubstituted; multicyclic ring systems (e.g. bi-, tri-tetra-etc. ring systems) which may be saturated, unsaturated or, and which may be substituted or unsubstituted, and may comprise one or more aromatic rings; etc. Particular examples of R1 groups include but are not limited to: methyl, ethyl, phenyl, substituted phenyl (e.g. substituted with a halogen, with methoxy, ethoxy, hydroxyl, etc.), thiophene, etc. In some aspects, R1 is absent.

Exemplary R2 functional groups include but are not limited to: lower alkyl groups (e.g. about C1 to about C5 carbons), which may be branched or unbranched, and may be substituted or unsubstituted; lower alkenes (e.g. about C1 to about C5) which may be branched or unbranched, and may be substituted or unsubstituted; 5 and 6 membered carbon rings which may be saturated or unsaturated, substituted or unsubstituted, and may be aromatic; multicyclic ring systems (e.g. bi-, tri-tetra-etc. ring systems) which may be saturated, unsaturated, and which may be substituted or unsubstituted, and may comprise one or more aromatic rings; etc. Examples of particular R2 functional groups include but are not limited to: methyl and phenyl. In some aspects, R2 may be absent, with the caveat that both R1 and R2 may not be absent. In other aspects, R1 and R2 may be atoms in a 5 or 6-membered ring or a multicyclic (e.g. bi-, tri-, tetra-, etc.) ring system. The ring or ring system may be aliphatic (e.g. pentyl, hexyl, decane, etc.), or may be aromatic (e.g. cyclopentadiene, substituted cyclopentdiene such as furan, pyrole etc., phenyl, substituted phenyl such as phenyl substituted with one or more halogens, methoxy, ethoxy, hydroxyl, etc.). The ring system may be a bicyclic ring system that is aliphatic or aromatic (e.g. decalin, naphthalene, tetralin etc.) which is substituted or unsubstituted. Suitable atoms or groups of atoms which may be included in substituted alkyl chains and rings include but are not limited to: N, S, O, CO, OCO, OEtO, halogens, etc.

X represents a halide functional such as F, Cl, Br, or I for example.

$R_3$ is preferably an electron withdrawing group selected from a nitrile, a carboxylic acid, a carboxylate, and a sulfoxide.

The alkylidene nitrile starting ingredient may be selected from many different alkylidene nitriles, which are generically represented in Table 1 as compound 1. Table 1 lists examples of alkylidene nitriles that may be used, but the list is in no way limited to these examples. Compounds 1a-1n are more specific species of compound 1. Compound 3 is a generic 2-halonicotinonitrile that is prepared by performing scheme 2 using compound 1. Likewise, compounds 3a-3n are the 2-halonicotinonitrile that correspond to 1a-1n, respectively.

Scheme 2 may be executed to make a diverse number of 2-halonicotinonitriles. In practice, one selects an alkylidene nitrile with the R1 and R2 functional groups that one desires to have as substituents on the 2-halonicotinonitrile end product. The halide is placed on the 2-halonicotinonitrile by selecting the appropriate halide donor.

TABLE 1

Examples of alkylidene nitriles and corresponding 2-halonicotinonitriles

| Alkylidene nitriles | 2-halonicotinonitriles |
|---|---|
| 1 | 3 |
| 1a | 3a |
| 1b | 3b |

TABLE 1-continued
Examples of alkylidene nitriles and corresponding 2-halonicotinonitriles
| Alkylidene nitriles | 2-halonicotinonitriles |
|---|---|
| 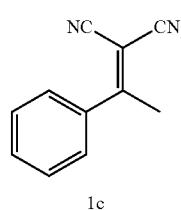 1c | 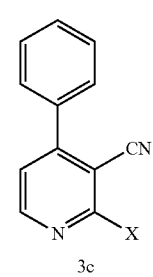 3c |
| 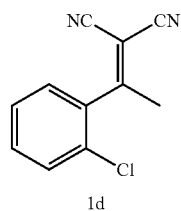 1d | 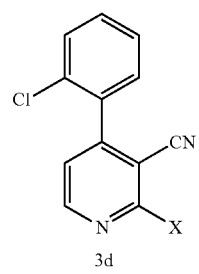 3d |
| 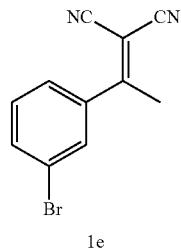 1e | 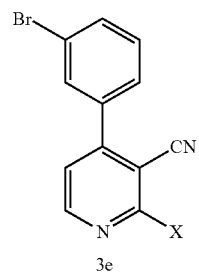 3e |
| 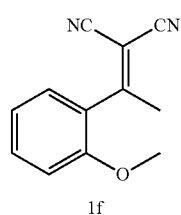 1f | 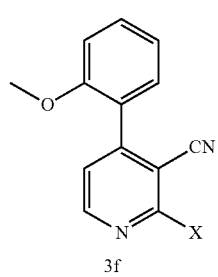 3f |
| 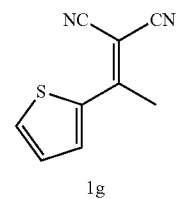 1g | 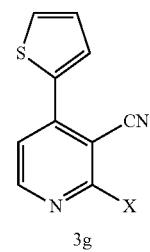 3g |
TABLE 1-continued
Examples of alkylidene nitriles and corresponding 2-halonicotinonitriles
| Alkylidene nitriles | 2-halonicotinonitriles |
|---|---|
| 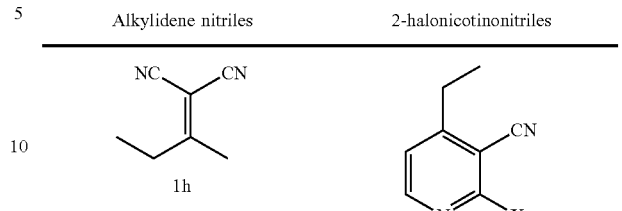 1h | 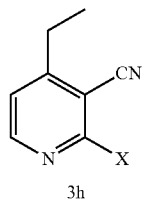 3h |
| 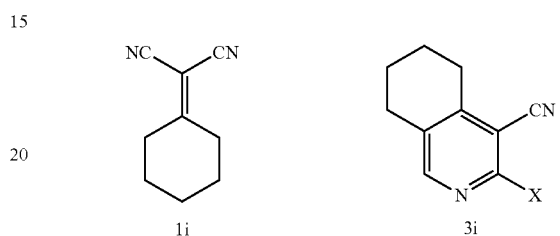 1i | 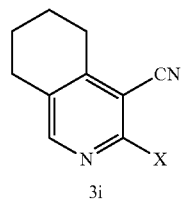 3i |
| 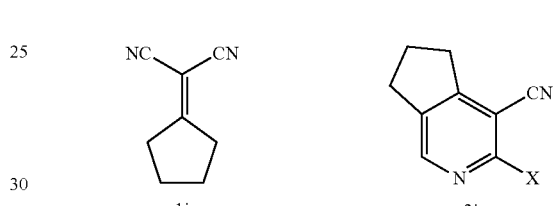 1j | 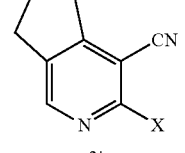 3j |
| 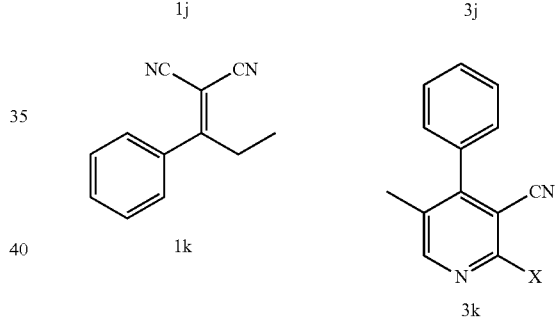 1k | 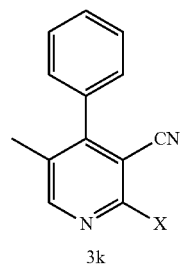 3k |
| 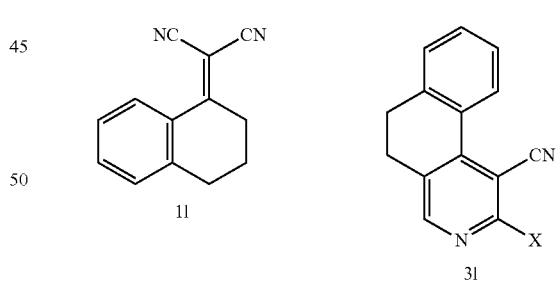 1l | 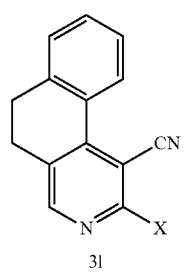 3l |
| 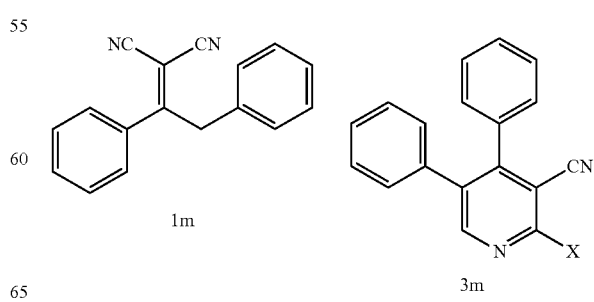 1m | 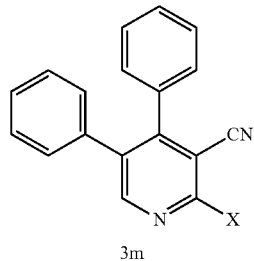 3m |

TABLE 1-continued

Examples of alkylidene nitriles and corresponding 2-halonicotinonitriles

| Alkylidene nitriles | 2-halonicotinonitriles |
|---|---|
| 1n (NC, CN structure) | 3n (CN, X pyridine structure) |

Use of a dehydrating agent in the initial step of Scheme 2 is advantageous because the dehydrating agent substantially retards dimerization of the alkylidene nitrile. By substantially retarding dimerization of the alkylidene nitrile, the yield of the enamine intermediate is improved relative to the BRP synthesis. Examples of dehydrating agents that may be used include, but are not limited to, at least one dehydrating agent selected from an anhydride, an acetyl chloride, an aluminum trichloride, a thionyl chloride, a trialkyl arylsilyl chloride, and an alkylarylsilyl chloride.

The C1-compound is a single carbon organic compound. Examples of C1-compounds that may be used include, but are not limited to, at least one compound selected from N,N-dimethylformamide dimethylacetal (DMF-DMA), a formate, a formaldehyde, N,N-dimethylformamide methyl methylsufonylacetal, methyl formate, and carbon monoxide.

The amount of C1-compound utilized may vary depending on the particular set of reactants used. It is sometimes advantageous, however, to use a stoichiometric excess of C1-compound relative to the alkylidene nitrile. The experimental data show that using a stoichiometric excess of C1-compound provides favorable % yields of the enamine and the 2-halonicotinonitrile.

A variety of conventional organic solvents may be used. Examples of these organic solvents include, but are not limited to, at least one organic solvent selected from dichloromethane, toluene, tetrahydrofuran, an ether, ethyl acetate, and chloroform.

Likewise, a variety of different halide donors may be used. Examples of these halide donors include, but are not limited to, at least one halide donor selected from a hydrogen halide, an alkyl halide, and a silyl halide.

The amount of dehydrating agent sufficient to substantially retard dimerization of the alkylidene nitrile will depend on the reactants being used. A preferred amount is 10 mol % to 200 mol %, 10 mol % to 100 mol %, 10 mol % to 50 mol %, or 10 mol % to 30 mol % of dehydrating agent.

The method may be executed by performing each step individually under batch conditions or by performing one or more steps under flow conditions. Under batch conditions, the method is executed in discrete steps by running the reactions in individual batches. Under flow conditions, the method is executed continuously or semi-continuously by running the reactions in one or more successive flow reactors in which the product of a preceding reaction flows into a subsequent flow reactor and becomes a reactant in a subsequent reaction. Executing the method under flow conditions often produces the 2-halonicotinonitrile faster than batch conditions.

Under batch conditions, a chemical reaction is performed in a batch reactor such as test-tube, flask, beaker, or the like. When step in a synthetic method are performed under batch conditions, the reaction products are removed from the batch reactor and, if desired, isolated and/or purified. When the procedure is carried out in industry, batch chemistry can be performed in a larger reactor with more reactants.

Under flow conditions, a chemical reaction is performed by passing reagents in a continuously flowing stream through devices containing small-dimensional channels such as coils, tubes, or the like. For example, pumps may force reactants into a tube where the first reaction occurs. The reaction products may then proceed to another tube and function as a reactant in another reaction. Microreactors are often used in flow chemistry. Under flow conditions, reactants and products may flow continuously from one reaction step to the next without an intervening isolation or purification step.

When executing the method under flow conditions, one may use one or more flow reactors. A flow reactor is a vessel, tube, container, or the like through which chemical reactants flow as a reaction proceeds from beginning to end. Each flow reactor includes a receiving end that receives the reactants and an output end that output the reaction product(s). The output end is spaced distally from the receiving end.

One or more of the flow reactors may contain a drying agent to substantially reduce the amount of water that flows from a preceding reaction to a subsequent reaction. When synthesizing an alkylidene nitrile from a ketone and a nitrile it may be desirable to include a drying agent in the flow reactor to remove water when Knoevangel condensation occurs.

Drying agents that may be used include substantially dry air, desiccants, and porous particulate matter that absorbs water. More specifically, the drying agent may be, but is not limited to, at least one drying agent selected from $Al_2O_3$, $SiO_2$, a molecular sieve, dry air, CaO, $CaCO_3$, and salt water.

A more particular embodiment of the method is now described. This embodiment, which is generally illustrated in Scheme 3, is a method of making the 2-halonicotinonitrile represented by compound 3a using compound 1a, an alkylidene malononitrile, as the alkylidene nitrile.

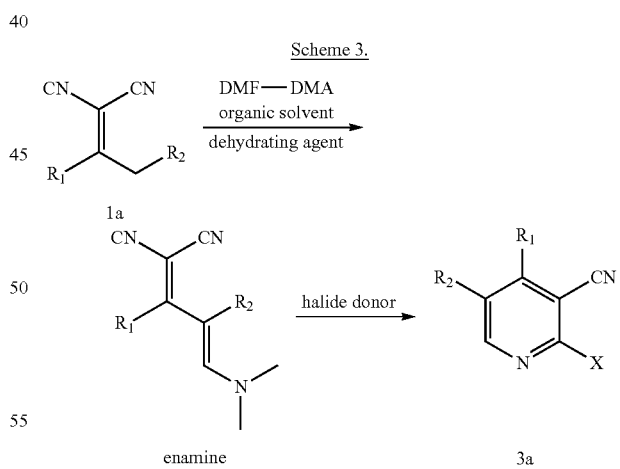

Scheme 3.

Compound 1a is reacted with the C-1 source N,N-dimethylformamide dimethylacetal (DMF-DMA) in a solution containing the organic solvent and sufficient dehydrating agent to substantially retard dimerization of compound 1a, thereby forming the enamine intermediate. The enamine intermediate is cyclized using the halide donor to form compound 3a.

Compound 3b where X=Br is called 2-bromo-4-methylnicotinonitrile. 2-bromo-4-methylnicotinonitrile is a particularly important 2-halonicotinonitrile because it can be used for making pharmaceuticals such as nevirapine. Nevirapine is made by reacting 2-chloro-3-amino-4-picoline (CAPIC) with 2-cyclopropylaminonicotinic acid (2-CAN) according to Scheme 4.

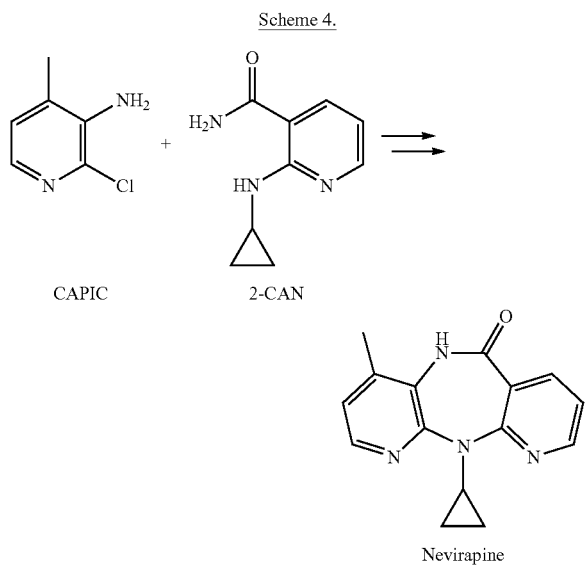

Scheme 4.

CAPIC   2-CAN

Nevirapine

In yet another particular embodiment of the method, Scheme 3 is performed as described above to make 2-bromo-4-methylnicotinonitrile using compound 1b as the alkylidene malononitrile and acetic anhydride as the dehydrating agent. This embodiment is advantageous for several reasons. First, it produces 2-bromo-4-methylnicotinonitrile in high yield because acetic anhydride retards dimerization of compound 1b. Second, it allows one to begin with the common chemicals acetone and malononitrile to make compound 1b and bypasses a step in the conventional synthesis strategy for CAPIC that produces a pyridone intermediate. One may form CAPIC from 2-bromo-4-methylnicotinonitrile by substituting the nitrile group for an amine group at the 3-position.

An additional embodiment is a flow-based method of making a 2-halonicotinonitrile (compound 3). In this flow-based method, a 2-halonicotinonitrile is synthesized by flowing acetone and malononitrile through a first flow reactor containing a drying agent to make compound 1a.

The enamine intermediate is prepared from reacting, by flowing through a second flow reactor, the alkylidene malononitrile, a C1-compound, an organic solvent, and sufficient dehydrating agent to substantially retard dimerization of the alkylidene malononitrile during the reaction.

The enamine intermediate is then cyclized using a halide donor, thereby forming compound 3a.

Referring to FIG. 1, the first flow 10 reactor receives the ketone and malononitrile at a first flow reactor receiving end 12 and outputs the alkylidene malononitrile at a first flow reactor output end 14, which is spaced distally from the first flow reactor receiving end 12. The second flow reactor receives the alkylidene malononitrile at a second flow reactor receiving end 22 and outputs the enamine intermediate at a second flow reactor output end 24 spaced distally from the second flow reactor receiving end 22. A third flow reactor 30 receives the enamine intermediate from second flow reactor output end 24 at a third flow reactor input end 32 and outputs the a 2-halonicotinonitrile at a third flow reactor output end 34 spaced distally from the third flow reactor receiving end 32.

EXAMPLES

This section provides specific examples of the method and various aspects thereof. These examples are provided to illuminate certain preferred aspects and embodiments, but the scope of the possible aspects and embodiments is not limited to what these examples teach.

Example 1: Acetic Anhydride Retards Dimerization of the Alkylidene Malononitriles This example shows that a dehydrating agent such as acetic anhydride retards dimerization of the alkylidene nitrile, starting material. Compound 5 was synthesized by performing the reaction illustrated in Scheme 5.

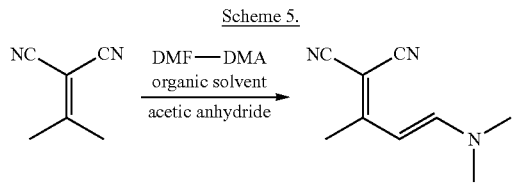

Scheme 5.

1b           5

The concentration (mol %) of acetic anhydride was varied to determine the amount of acetic anhydride needed to retard dimerization of compound 1b, which would thereby result in a high % yield of compound 5. The organic solvent was 0.1 M dry dichloromethane (DCM). The reaction ran for about 17 hours and was performed at a 0.5 mmol scale. The results are summarized in Table 2.

TABLE 2

% Yield compound 5

| Run | Ac$_2$O (mol %) | DMF-DMA equiv. | % Yield[a] |
|---|---|---|---|
| 1 | 0 | 1 | 44 |
| 2 | 200 | 1 | 84 |
| 3 | 100 | 1 | 86 |
| 4 | 50 | 1 | 88 |
| 5 | 25 | 1 | 89 |
| 6 | 20 | 1 | 89 |
| 7 | 10 | 1 | 90 |
| 8 | 20 | 1.2 | >99 |

[a]Calibrated yields determined by gas chromatography.

One of the objectives of this experiment was to determine how little acetic anhydride could be used while still achieving high yields. At 10 mol % acetic anhydride, the yield was 90%. By using 20 mol % acetic anhydride and adjusting the DMF-DMA equivalents from 1 to 1.2, the yield was >99%.

Toluene was determined to be a good solvent for the reaction because, when toluene was used, compound 5 precipitated. Toluene was tested at concentrations from 0.1 M to 1 M. Precipitation of compound 5 drove the reaction forward and allowed for isolation of compound 5 by filtration. When the reaction ran at room temperature, the yield was 81%.

Scheme 5 was repeated several times at different temperatures using 20 mol % acetic anhydride and 1.2 DMF- DMA equivalents in 1M dry toluene to determine whether the amount of enamine formed depended on the temperature. The reactions were performed at 20 mmol scale. The results are summarized in Table 3.

TABLE 3

Temperature dependence on enamine formation

| Run | Temperature (° C.) | % Yield[a] |
|---|---|---|
| 1 | room temperature | 81 |
| 2 | 35 | 90 |
| 3 | 45 | 94 |
| 4 | 60 | 78 |

[a]Isolated yields.

The yield of compound 5 substantially improved when the temperature was raised from about 35 to about 45 Celsius.

Example 2: Synthesis of Nicotinonitriles Using Scheme 2

This examples shows that Scheme 2 may be used to synthesize many different 2-halonicotinonitriles.

In one set of experiments, brominated versions compounds 3b-3g were synthesized beginning from compounds 1b-1g using 0.1 M dichloromethane as the organic solvent and HBr as the halogen halide. The HBr was present as 33% HBr in acetic acid. To produce the enamine intermediate from the alkylidene malononitrile, 20 mol % acetic anhydride and 1.2 equivalents DMF-DMA were used. The reactions took place over about 16 to about 24 hours and were performed at 5 mmol scale. The results of this set of experiments are summarized in Table 4.

TABLE 4

Examples of 2-halonicotinonitriles synthesized in 0.1M DCM

| Run | Alkylidene nitrile | 2-halonicotinonitrile | % Yield[a] |
|---|---|---|---|
| 1 | 1b | 3b | 91[b] |
| 2 | 1c | 3c | 94 |
| 3 | 1d | 3d | 87 |
| 4 | 1e | 3e | 97 |
| 5 | 1f | 3f | 87 |
| 6 | 1g | 3g | 94 |

[a]Isolated yields from the corresponding alkylidene malononitrile. Samples still contained <1 wt % acetic acid.
[b]Performed at 20 mmol scale.

In another set of experiments, brominated versions compounds 3b and 3h-3n were synthesized beginning from compounds 1b and 1h-1n using 1 M toluene as the organic solvent and HBr as the halide donor. The HBr was present as 33% HBr in acetic acid. To produce the enamine intermediate from the alkylidene malononitrile, 20 mol % acetic anhydride and 1.2 equivalents DMF-DMA was used. The reactions took place over about 1 to about 18 hours and were performed at 5 mmol scale. The results of this set of experiments are summarized in Table 5.

TABLE 5

Examples of nicotinonitriles synthesized in 1M toluene

| Run | Alkylidene nitrile | 2-halonicotinonitrile | % Yield[a] |
|---|---|---|---|
| 1 | 1b | 3b | 76[b] |
| 2 | 1h | 3h | 32[c] |
| 3 | 1i | 3i | 69 |
| 4 | 1j | 3j | 73 |
| 5 | 1k | 3k | 82[d] |
| 6 | 1l | 3l | 81 |
| 7 | 1m | 3m | 74 |
| 8 | 1n | 3n | <1[e] |

[a]Isolated yields from the corresponding alkylidene nitrile. Samples still contained <1 wt % acetic acid.
[b]Yield improved to 83% when scaled to a 20 mmol reaction.
[c]Contained <1% of the 2-bromo-4,5-dimethylnicotinonitrile isomer.
[d]Contained 2 wt % of compound 1k.
[e]Compound 5n was not isolated.

Run 8 in Table 5 was an anomaly. The reaction may not have worked well in run 8 because compound 1n was derived from an aldehyde, whereas the other alkylidene malononitriles tested were derived from ketones.

Both sets of experiments show that Scheme 2 may be used to make many different 2-halonicotinonitriles with a yield of at least about 50%.

In yet another set of experiments, the 2-chloro and 2-iodo nicotinonitrile versions of compound 3b were synthesized the from the enamine compound 5. To synthesize the 2-chloro-4-methylnicotinonitrile, HCl gas was used in place of HBr. To synthesize 2-iodo-4methylnicotinonitrile, trimethylsilyl iodide (TMSI) was blended with compound 5 in acetic acid and water to produce HI in situ. Having an iodo functional group present on the nicotinonitrile is useful for coupling transition metals to the 2-halonicotinonitrile.

Example 3: Semi-Continuous Synthesis of 2-Bromo-4-Methylnicotinonitrile Using Scheme 3

This example describes a flow-based method for making 2-bromo-4-methylnicotinonitrile, an example of a 2-halonicotinonitrile.

Acetone and malononitrile were reacted in a twin packed-bed flow reactor to make compound 1b. A first column in the flow reactor contained basic $Al_2O_3$ particulates to catalyze the reaction. A second column in the flow reactor contained powdered 3 Angstrom molecular sieve to act as the drying agent and prevent substantial decomposition of the DMF-DMA used downstream.

The temperature of the columns and residence times of in the coil were varied to determine suitable reaction conditions. The reactant concentrations were 2 M. Table 6 summarizes the results.

TABLE 6

Results from varying reaction conditions to make compound 1b from acetone and malononitrile

| Run | $Al_2O_3$ Column Temp. (° C.) | 3 Å MS Column Temp. (° C.) | Residence Time of Coil | % Yield[a] |
|---|---|---|---|---|
| 1 | 25 | 20 | 2 | N/A[b] |
| 2 | 25 | 20 | 4 | 91 |
| 3 | 20 | 25 | 4 | 91 |
| 4 | 10 | 25 | 4 | 92 |
| 5 | 35 | 20 | 4 | 88 |
| 6 | 50 | 20 | 4 | 88 |
| 7 | 75 | 20 | 4 | 84 |

TABLE 6-continued

Results from varying reaction conditions to make
compound 1b from acetone and malononitrile

| Run | $Al_2O_3$ Column Temp. (° C.) | 3 Å MS Column Temp. (° C.) | Residence Time of Coil | % Yield[a] |
|---|---|---|---|---|
| 8 | 95 | 20 | 4 | 81 |
| 9 | 95 | 20 | 6 | 81 |

[a]Determined with GC using mesityline as an internal standard,
[b]The fast flow rate needed for this residence time made the pressure exceed the maximum limit.

The preferred conditions were obtained from run 3.

Compound 5 was synthesized in a second flow reactor. Because compound 5 is very soluble in dichloromethane, dichloromethane was used as the organic solvent. The flow reactor was sealed to allow pressure to build therein when the coil in the flow reactor was heated above the boiling point of dichloromethane. By running the reaction at 1 M concentration and heating the coil to 95 Celsius, compound 5 was obtained at >93% yield with a two minute residence time. This allowed for compound 5 to be made in about 1/30 the time it took under batch conditions.

2-bromo-4-methylnicotinonitrile was synthesized from compound 5 by replicating flow conditions in a round bottom flask. Acetic acid and HBr were placed in the flask and 25 mL of the resulting 1 M reaction solution from the previous step was added. The solution was stirred for about 45 minutes at 55 Celsius to allow compound 5 to cyclize into 2-bromo-4-methylnicotinonitrile.

Among the reaction conditions tested, the following were the most preferred. Compound 1b was made using 0.5 M reaction. Compound 5 was made by heating the $Al_2O_3$ column to 95 Celsius and the molecular sieve column to 20 Celsius. 0.2 equivalents of acetic anhydride and 1.45 equivalents DMF-DMA were used. The reaction solution containing compound 5 was added directly to a solution of acetic acid and HBr. The average yield of 2-bromo-4-methylnicotinonitrile was about 69%.

This disclosure describes preferred embodiments, but not all possible aspects and embodiments of the methods. Where a particular feature is disclosed in the context of a particular method, that feature can also be used, to the extent possible, in combination with and/or in the context of other embodiments of the methods. The methods may be embodied in many different forms and should not be construed as limited to only the embodiments described here.

That which is claimed is:

1. A method of making a 2-halonicotinonitrile, the method comprising:
    (a) reacting an alkylidene nitrile having the formula

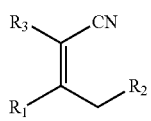

with a C1-compound in an organic solvent and sufficient dehydrating agent to substantially retard dimerization of the alkylidene nitrile during the reaction, thereby forming an enamine intermediate; and
    (b) cyclizing the enamine intermediate with a gaseous halide (X) donor, thereby forming a 2-halonicotinonitrile having the formula

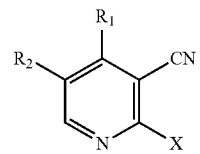

wherein
    i) R1 is methyl, ethyl, phenyl, methoxyphenyl, halogen substituted phenyl or thiophene and R2 is absent or is methyl or phenyl, or
    ii) R1 and R2 are atoms in a 5- or 6-membered aliphatic ring or a tetralin bicyclic ring system,
    iii) R3 is CN,
    iv) the dehydrating agent is an anhydride, and
    vi) the C1-compound is dimethylformamide dimethyl acetal.

2. The method of claim 1, wherein the dehydrating agent is acetic anhydride.

3. The method of claim 1, wherein the organic solvent is selected from dichloromethane, toluene, tetrahydrofuran, an ether, ethyl acetate, and chloroform.

4. The method of claim 1, wherein the gaseous halide donor is selected from a hydrogen halide, an alkyl halide, and a silyl halide.

5. The method of claim 1, wherein X is Br, Cl, or I.

6. The method of claim 1, wherein sufficient dehydrating agent to substantially retard dimerization of the alkylidene nitrile during the reaction is 10 mol % to 200 mol % of dehydrating agent.

7. The method of claim 1, wherein the C1-compound is present in stoichiometric excess relative to the alkylidene nitrile.

8. The method of claim 1, wherein sufficient dehydrating agent to substantially retard dimerization of the alkylidene nitrile during the reaction is 10 mol % to 50 mol % of dehydrating agent; and the C1-compound is present in stoichiometric excess relative to the alkylidene nitrile.

9. A method of making a 2-halonicotinonitrile, the method comprising:
    (a) reacting an alkylidene malononitrile having the formula

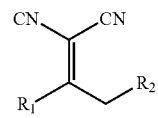

with N,N-dimethylformamide dimethylacetal in a solution containing an organic solvent and sufficient dehydrating agent to substantially retard dimerization of the alkylidene malononitrile during the reaction, thereby forming an enamine intermediate; and
    (b) cyclizing the enamine intermediate with a gaseous halide (X) donor, thereby forming a 2-halonicotinonitrile having the formula

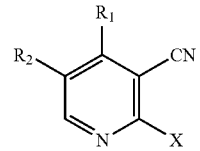

wherein
 i) R1 is methyl, ethyl, phenyl, methoxyphenyl, halogen substituted phenyl or thiophene and R2 is absent or is methyl or phenyl, or
 ii) R1 and R2 are atoms in a 5- or 6-membered aliphatic ring or a tetralin bicyclic ring system, and
 ii) the dehydrating agent is an anhydride.

10. The method of claim 9, wherein the dehydrating agent is acetic anhydride.

11. The method of claim 9, wherein the organic solvent is selected from dichloromethane, toluene, tetrahydrofuran, an ether, ethyl acetate, and chloroform.

12. The method of claim 9, wherein the gaseous halide donor selected from a hydrogen halide, an alkyl halide, and a silyl halide.

13. The method of claim 9, wherein X is Br, Cl, or I.

14. The method of claim 9, wherein sufficient dehydrating agent to substantially retard dimerization of the alkylidene malononitrile during the reaction is 10 mol % to 200 mol % of dehydrating agent.

15. The method of claim 9, wherein the N,N-dimethylformamide dimethylacetal is present in stoichiometric excess relative to the alkylidene malononitrile.

16. The method of claim 9, wherein sufficient dehydrating agent to substantially retard dimerization of the alkylidene malononitrile during the reaction is 10 mol % to 50 mol % of dehydrating agent; and the N,N-dimethylformamide dimethylacetal is present in stoichiometric excess relative to the alkylidene nitrile.

17. A method of making a 2-bromo-4-methylnicotinonitrile, the method comprising:
 (a) reacting an alkylidene malononitrile having the formula

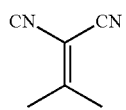

with N,N-dimethylformamide dimethylacetal in a solution containing an organic solvent and sufficient acetic anhydride to substantially retard dimerization of the alkylidene malononitrile during the reaction, thereby forming an enamine intermediate; and
 (b) cyclizing the enamine intermediate with a gaseous bromide donor, thereby forming a 2-bromo-4-methylnicotinonitrile having the formula

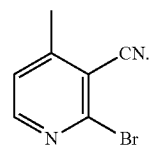

18. The method of claim 17, wherein the organic solvent is at least one organic solvent selected from dichloromethane, toluene, tetrahydrofuran, an ether, ethyl acetate, and chloroform.

19. The method of claim 17, wherein the gaseous bromide donor is at least one gaseous bromide donor selected from a hydrogen bromide and an alkyl bromide.

20. The method of claim 17, wherein sufficient acetic anhydride to substantially retard dimerization of the alkylidene malononitrile during the reaction is 10 mol % to 200 mol % of acetic anhydride.

21. The method of claim 17, wherein the N,N-dimethylformamide dimethylacetal is present in stoichiometric excess relative to the alkylidene malononitrile.

22. The method of claim 17, wherein: sufficient acetic anhydride to substantially retard dimerization of the alkylidene malononitrile during the reaction is 10 mol % to 50 mol % of dehydrating agent; and the N,N-dimethylformamide dimethylacetal is present in stoichiometric excess relative to the alkylidene nitrite.

* * * * *